United States Patent [19]

Shirley et al.

[11] Patent Number: 4,539,988

[45] Date of Patent: Sep. 10, 1985

[54] DISPOSABLE AUTOMATIC LANCET

[75] Inventors: Gaylord R. Shirley, Delray Beach; Daniel J. Chiodo, Miami, both of Fla.

[73] Assignee: Packaging Corporation International, Hialeah, Fla.

[21] Appl. No.: 510,652

[22] Filed: Jul. 5, 1983

[51] Int. Cl.³ .............................................. A61B 17/32
[52] U.S. Cl. ................................ 128/314; 128/329 R
[58] Field of Search .............................. 128/314–315, 128/329 R; 30/367, 155, 159; 604/156–157, 136, 46, 47, 22

[56] References Cited

U.S. PATENT DOCUMENTS

| | | | |
|---|---|---|---|
| 3,760,809 | 9/1973 | Campbell, Jr. ........................ | 128/314 |
| 4,214,584 | 7/1980 | Smirnov et al. ...................... | 604/157 |
| 4,230,118 | 10/1980 | Holman et al. ..................... | 128/314 |
| 4,388,925 | 6/1983 | Burns ................................... | 128/314 |
| 4,414,975 | 11/1983 | Ryder et al. ......................... | 128/314 |
| 4,442,836 | 4/1984 | Meinecke et al. .................. | 128/314 |

Primary Examiner—C. Fred Rosenbaum
Assistant Examiner—Gene B. Kartchner
Attorney, Agent, or Firm—Oltman and Flynn

[57] ABSTRACT

A disposable automatic surgical lancet having a plastic spring arm molded integral with a central frame piece which is part of the housing. The free end of the spring arm carries a holder for a lancet blade or needle. The spring arm can be cocked in a retracted, stressed position from which it is released by pushing in on the front wall of the housing. When released, the spring arm carries the lancet blade or needle upward to project through an opening in a concave depression on the top of the housing where the patient's finger tip rests. A lock arrangement inside the housing holds the front wall in its pushed-in position so the lancet cannot be used again inadvertently.

18 Claims, 9 Drawing Figures

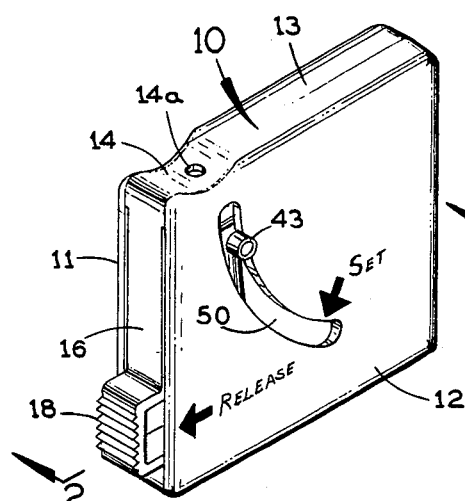
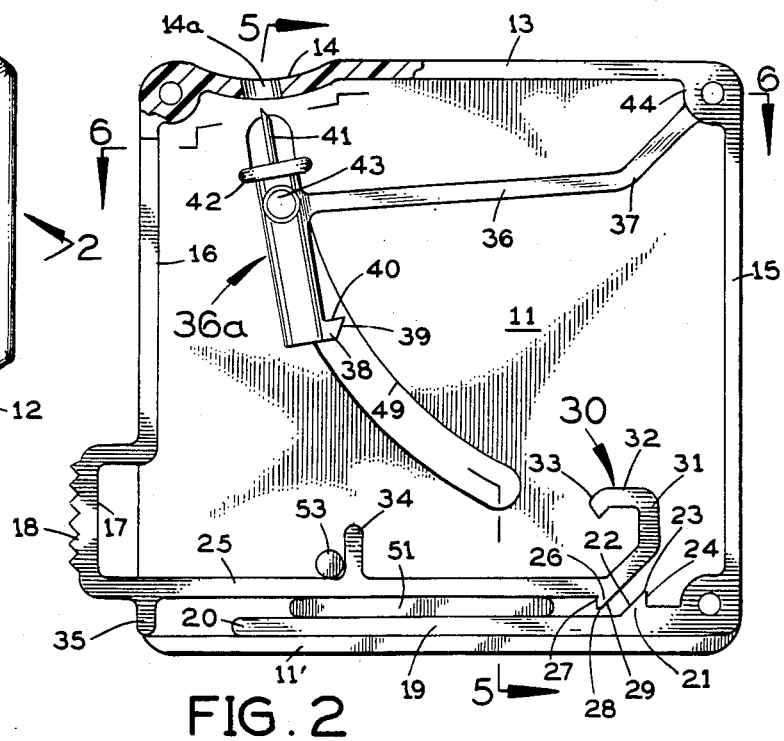
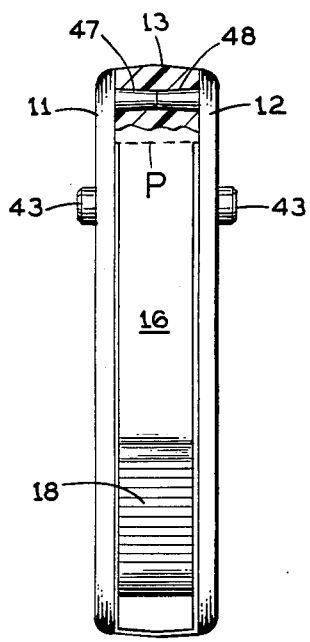
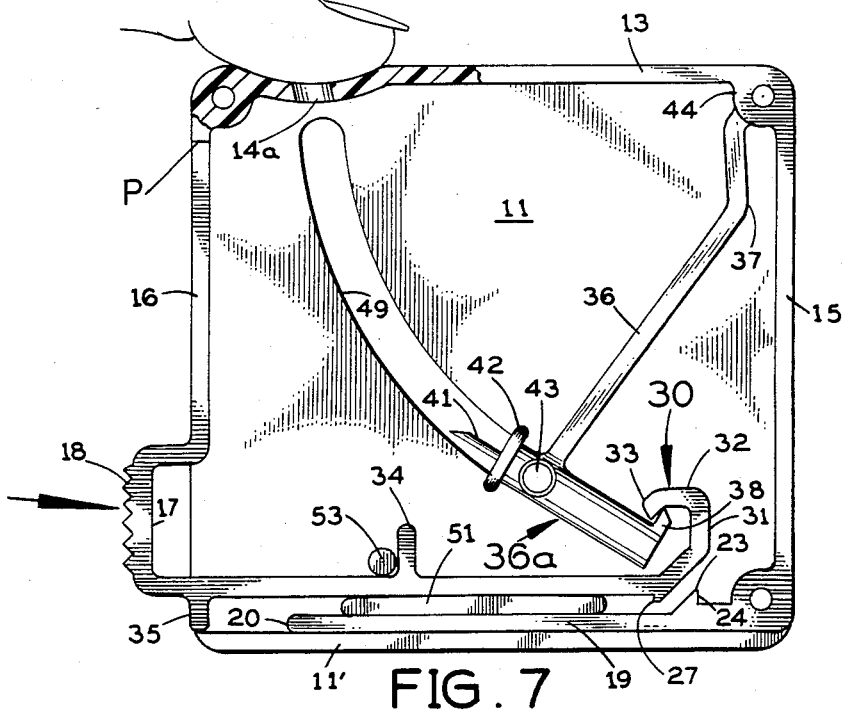

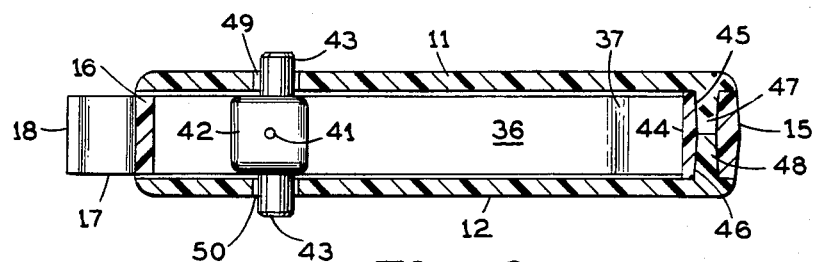
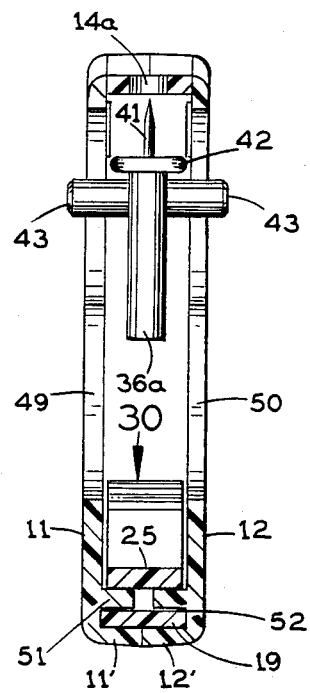
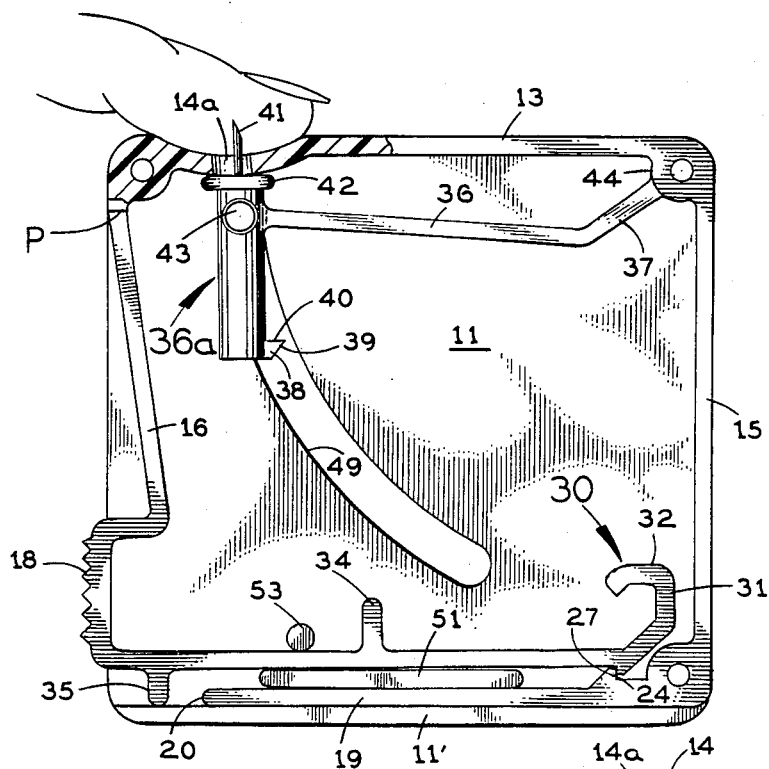
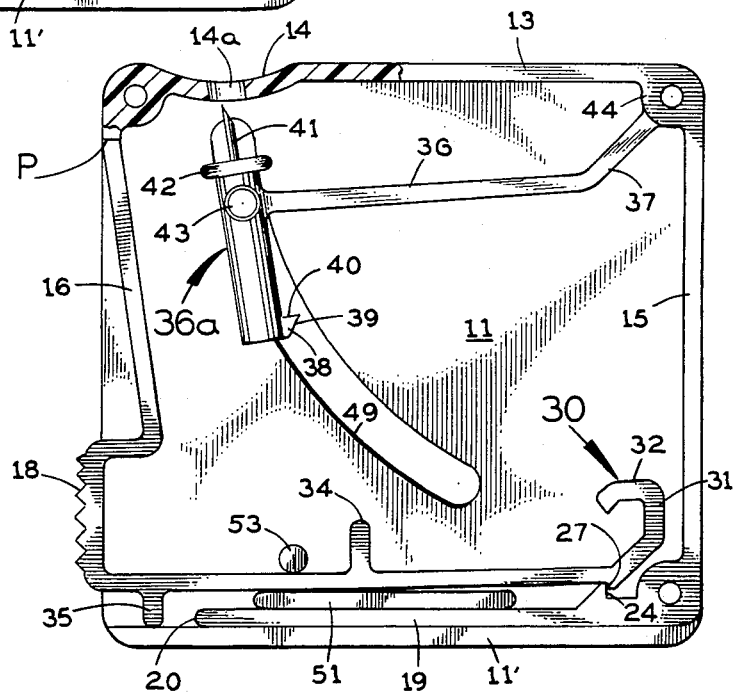

DISPOSABLE AUTOMATIC LANCET

SUMMARY OF THE INVENTION

This invention relates to a disposable automatic surgical lancet.

In the use of surgical lancets it is desirable to minimize any apprehension the patient may have about the procedure, as well as to make the procedure itself as safe and comfortable as possible. In accordance with the present invention, these objectives are achieved by enclosing the lancet blade in a housing having a seat for the patient's finger tip which is located on top of the housing. This alleviates the fear and nervousness of some patients who may feel more in control with his or her finger placed over the lancet housing than if the reverse were true. The lancet blade is on a spring arm which need not be cocked in retracted, stressed position until just before the lancing procedure is to take place, thereby reducing the possibility of accidental release of the spring arm from the cocked position. A manually operated release actuator on the housing holds the spring arm in its cocked position and then releases it when the actuator is pushed horizontally inward. Such movement of the actuator is hardly noticeable to the patient. After the release actuator is pushed in, it is locked in a retracted position which insures that the lancet cannot be used again because even if the spring arm were moved again into its cocked position, the release actuator would not hold it there.

A principal object of this invention is to provide a novel automatic surgical lancet which is intended for use only once and then thrown away.

Another object of this invention is to provide such a lancet which is constructed to minimize any discomfort or apprehension the patient may feel.

Another object of this invention is to provide a novel lancet having a lancet blade on a spring arm which may be cocked in a stressed position and then released from that position so unobtrusively that the pricking of the patient's finger may be over before the patient realizes what is happening.

Another object of this invention is to provide a novel lancet having a lancet blade on a spring arm which need not be cocked until just before the pricking operation is to take place.

Further objects and advantages of this invention will be apparent from the following detailed description of a presently preferred embodiment which is illustrated schematically in the accompanying drawings.

DESCRIPTION OF THE DRAWINGS

FIG. 1 is a front perspective view of the present invention;

FIG. 2 is a vertical longitudinal section taken along the line 2—2 in FIG. 1;

FIG. 3 is a top plan view;

FIG. 4 is a front elevation, with one part broken open for clarity;

FIG. 5 is a vertical cross-section taken along the line 5—5 in FIG. 2;

FIG. 6 is a horizontal cross-section taken along the line 6—6 in FIG. 2;

FIG. 7 is a view similar to FIG. 2 but showing the spring arm cocked;

FIG. 8 is a view similar to FIG. 7 and showing the position of parts after the spring arm has been released and has carried the blade to the limit of its finger-pricking movement; and FIG. 9 is a view similar to FIG. 8 and showing the spring arm and lancet blade after they have rebounded.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION

Referring to FIG. 1, the present invention comprises a central frame piece 10 and opposite side pieces 11 and 12 engaging the frame on opposite sides. The central piece preferably is molded of polypropylene or nylon.

Referring to FIG. 2, the central frame piece 10 has a generally flat horizontal top wall 13 with a concave recess or depression 14 toward its front end, which is the left end in this Figure. The patient's finger will rest here directly above an opening 14a, as shown in FIG. 7. A vertical flat back wall 15 extends down from the top wall 13 at its right end in FIG. 2, and a vertical flat front wall 16 extends down from the top wall 13 at its left end in this Figure. At its lower end the front wall 16 carries a forwardly offset vertical segment 17 with a serrated front face 18 for engagement by the thumb or forefinger of the person operating the lancet.

The central frame piece has a bottom wall 19 joined to the lower end of its back wall 15 and extending forward horizontally. The bottom wall 19 terminates in a rounded front edge 20 located in vertically spaced relation below the depression 14 in the top wall 13 of the central frame piece and behind the vertical plane of its front wall 16. Toward its back end the bottom wall 19 is formed with an upwardly projecting locking tooth 21 having an upwardly and rearwardly inclined front face 22, a short horizontal top face 23, and a vertical back face 24 extending down from the top face 23 and defining a locking shoulder on the back of the tooth 21.

The central frame piece has a generally horizontal wall 25 which extends rearward from the lower end of the forwardly offset segment 17 at the lower end of its front wall 16. For most of its length this wall 25 is spaced a short distance above the bottom wall 19. Toward its back end the wall 25 presents a downwardly projecting locking tooth 26 having a vertical front face 27, a short horizontal bottom face 28 extending rearward from the lower end of its front face, and an upwardly and rearwardly inclined back face 29. When the forwardly offset segment 17 of the front wall 16 is pushed in (i.e., rearward), the inclined back face 29 of the depending locking tooth 26 on wall 25 slides up across the inclined front face 22 of the locking tooth 21 on bottom wall 19. Then the bottom face 28 of tooth 26 slides rearward across the top face 23 of tooth 21 until the locking tooth 26 on wall 25 can drop behind the locking tooth 21 on bottom wall 19, with the vertical front face 27 of tooth 26 engaging the vertical rear face 24 of tooth 21, as shown in FIG. 8.

The back end of wall 25 is formed with a generally hook-shaped finger 30 having an upwardly extending vertical rear segment 31, a horizontal top segment 32 extending forward from the upper end of rear segment 31, and a forwardly and downwardly inclined segment 33 at the front end of top segment 32.

About midway along its length from front to back, the wall 25 is formed with an upwardly projecting vertical segment 34.

Near its front end, the wall 25 has a downwardly projecting vertical segment 35 which is vertically aligned with the front wall 16.

The central frame piece 10 also has a flexible and resilient spring arm 36 which is molded integrally with the remainder of this frame piece, as already described. This spring arm has its upper end integrally joined to the top rear corner of the central frame piece where the top wall 13 is joined to the back wall 15. The spring arm 36 is molded with a bend at 37 a short distance down from its attached end, and in its unstressed condition the spring arm 36 will be positioned as shown in FIG. 2.

The front end of spring arm 36 (which is the left end in FIG. 2) is free to move. At this end the spring arm is formed with a lancet blade holder 36a which extends substantially perpendicular to the remainder of spring arm 36 and projects above and below it. The lower end of the blade holder 36a has a rearwardly projecting locking tooth 38 with an upwardly and rearwardly inclined back face 39 and a flat top face 40 extending forward from the upper end of the back face 39 at an acute angle to it. When the free end of the spring arm 36 is displaced downward and rearward from the normal, unstressed position (FIG. 2) to a cocked position (FIG. 7), the inclined back face 39 of the locking tooth 38 on the bottom of the lancet blade holder 36a slides down across the front edge of the inclined front segment 33 of locking finger 30 until the top face 40 of locking tooth 38 engages behind segment 33. In this position of the parts, the locking finger 30 holds the spring arm 36 in a stressed, cocked position until the forwardly offset segment 17 at the front of frame piece 10 is pushed rearward (FIG. 8) to retract the locking finger 30 out of engagement with the locking tooth 38. When this release takes place, the preformed spring bias of spring arm 36 causes it to return toward the normal, unstressed position (FIG. 2) and to overtravel up beyond that position to the position shown in FIG. 8, after which the spring arm will rebound to its unstressed position (FIG. 9).

Above the free end of spring arm 36 the lancet blade holder 36a carries an upwardly projecting lancet blade or needle 41. As shown in FIG. 2, when the spring arm 36 is in its normal, unstressed position, the pointed upper end of the lancet blade 41 is spaced a short distance below the opening 14a in the recessed segment 14 of the top wall of the frame piece. After the spring arm 36 has been cocked (FIG. 7) and then released, in the over-travel of the spring arm up beyond its unstressed position the tip of the lancet blade 41 passes up through the opening 14a and above the top surface at 14 so as to penetrate the patient's finger tip to a suitable depth, as shown in FIG. 8.

The lancet blade holder 36a has a transverse annular flange 42 which engages the bottom of the recessed segment 14 of top wall 13 around the opening 14a to define the upward limit of movement of the spring arm and the lancet blade, after which the spring arm rebounds to the unstressed position shown in FIG. 9.

A short distance below shoulder 41 the lancet blade holder 36a on the free end of spring arm 36 carries a horizontal cross pin 43 which projects on opposite sides of it (FIG. 5).

The opposite side pieces 11 and 12 of the device are mirror images of each other. Each of them is generally rectangular, with rounded corners, and is substantially flat for most of its extent.

As shown in FIG. 2, at the upper rear corner where the spring arm 36 is attached, the central frame piece 10 is formed with a rounded enlargment 44 at the corner between its top wall 13 and its back wall 15. This corner enlargement 44 is formed with tapered recesses 45 and 46 (FIG. 6), which extend inward from its opposite sides. These recesses adjoin one another at their inner ends to form a continuous opening. The side piece 11 is formed with a tapered projection 47 on the inside which has a tight fit in recess 45 at the corner enlargement 44 of the central frame piece. Similarly, the opposite side piece 12 is formed with a tapered projection 48 on the inside which has a tight fit in recess 46 in the central frame piece.

At each of the top front and lower rear corners of the device, the central frame piece 10 has similar corner enlargments formed with recesses which tightly receive corresponding tapered projections on the side pieces 11 and 12 so that these side pieces are held snugly against the opposite sides of the central frame piece 10.

At their bottom edges, the opposite side pieces 11 and 12 have inturned horizontal flanges 11' and 12' (FIG. 5) which extend directly beneath the bottom wall 19 of central frame piece 10. A short distance above these bottom flanges the side pieces 11 and 12 are formed with inwardly protruding horizontal segments 51 and 52 (FIG. 5) located between the top face of bottom wall 19 and wall 25 of the central frame piece 10. A short distance above these segments 51 and 52, the opposite side pieces 11 and 12 are formed with inwardly protruding horizontal protrusions 53 (FIG. 2) of circular cross-section which extend closely across the top of wall 25, so that the movement of wall 25 is guided between the protrusions 53 above and segments 51 and 52 below. In the normal (unlocked) position of wall 25 its protrusion 34 engages the back of protrusions 53.

The opposite side pieces 11 and 12 are formed with aligned arcuate openings 49 and 50, respectively (FIGS. 1 and 2), which pass the cross pin 43 on the free end of spring arm 41 so that it can be retracted manually from the normal, unstressed position (FIG. 2) to the cocked position (FIG. 7), and after being released from the cocked position it can move up to the position shown in FIG. 8 and then back to the position shown in FIG. 9.

In this device, the offset lower end segment 17 of the front wall of frame piece 10, the horizontal wall 25 extending rearward from it, the locking tooth 26, and finger 30 constitute a release actuator for holding the spring arm 36 cocked (FIG. 7) and for releasing the spring arm in response to an inward push on the offset segment 17.

The front wall 16 is flexible enough at its upper end that it can pivot about a line P (FIG. 8) a short distance below the enlarged top front corner of the central frame piece 10 when its forwardly offset lower end segment 17 is pushed in. As shown in FIG. 4, the width of the front wall 16 is slightly reduced at this line P from its width above, where it extends from one side piece 11 over to the opposite side piece 12.

OPERATION

Normally, the parts of this automatic lancet are positioned as shown in FIG. 2.

Just before the lancing operation is to take place, the nurse or doctor pushes down on the exposed cross pin 43 to move the spring arm 36 down to the cocked position shown in FIG. 7. The arcuate slots 49 and 50 in the opposite side pieces 11 and 12 guide the cross pin 43 as the spring arm 36 is displaced to its cocked position. The locking tooth 38 on the lancet blade holder 36a slides into locking engagement with finger 30 of the release actuator. The release actuator 17,25,26,30 is held against forward displacement by the engagement of its vertical projection 34 against the back of the circular protrusions 53 on the side pieces 11 and 12.

The release actuator is retracted by pushing in on the forwardly offset lower end segment 17 on the front wall of the central frame piece, which causes wall 25, locking finger 26 and finger 30 to be displaced from the locking position (FIG. 7) to the right to the release position. During such movement the finger 30 disengages from the locking tooth 38 on the lancet blade holder 36a, freeing the spring arm 36 to move up clockwise from the cocked position shown in FIG. 7 to the position shown in FIG. 1, where the lancet blade 41 projects up through the opening 14a and pierces the patient's finger. The flange 42 on the lancet blade holder 36a strikes the depressed segment 14 of top wall 13 from below to limit this upward movement of the spring arm. After the finger 30 releases the spring arm, the locking tooth 26 on the release actuator slides up over the locking tooth 21 on bottom wall 19 until the vertical faces of these teeth engage each other, as shown in FIG. 8, to lock the release actuator in its pushed-in position. This prevents an inadvertent repeat operation of the lancet because even if the spring arm 36 is displaced again to its cocked position it would not be engaged and held there by finger 30 on the inner end of the release actuator because this finger now is retracted too far to engage the locking tooth 38 on the lancet blade holder 36a.

After the lancet blade 41 pierces the patient's finger to a predetermined safe depth, which is limited by the engagement of flange 42 on the lancet blade holder against the bottom face of the top wall 13 around the opening 14a, the spring arm 36 then rebounds to its normal, unstressed position (FIG. 9) in which the lancet blade 41 is retracted so as not to be engageable by a patient's finger. The release actuator 17,25,26,30 remains locked in its pushed-in, retracted position because of the locking engagement between its locking tooth 26 and the locking tooth 21 on bottom wall 25.

We claim:

1. An automatic surgical lancet comprising:
means defining a housing having a top wall with an upwardly-facing concave depression for receiving the tip of a patient's finger, said top wall having an opening at said depression for passing a lancet blade;
a spring arm inside said housing having a free end which is movable toward and away from said opening;
a release actuator for holding said spring arm cocked in a stressed position in which its free end is held away from said opening, said release actuator being located below said top wall of the housing and being manually operable to release said spring arm for movement of its free end up toward said opening;
a lancet blade holder on said free end of said spring arm;
and a lancet blade carried by said holder;
said release actuator being movable substantially horizontally to release the spring arm.

2. An automatic surgical lancet comprising:
means defining a housing having a top wall with an upwardly-facing concave depression for receiving the tip of a patient's finger, said top wall having an opening at said depression for passing a lancet blade;
a spring arm inside said housing having a free end which is movable toward and away from said opening;
a release actuator for holding said spring arm cocked in a stressed position in which its free end is held away from said opening, said release actuator being manually operable to release said spring arm for movement of its free end up toward said opening;
a lancet blade holder on said free end of said spring arm;
a lancet blade carried by said holder;
and means, operable upon completion of said manual operation of the release actuator to release the spring arm, for locking the release actuator in a disabled position in which it cannot again hold said spring arm cocked in said stressed position.

3. An automatic surgical lancet comprising:
means defining a housing having a top wall with an upwardly-facing concave depression for receiving the tip of a patient's finger, said top wall having an opening at said depression for passing a lancet blade;
a spring arm inside said housing having a free end which is movable toward and away from said opening;
a release actuator for holding said spring arm cocked in a stressed position in which its free end is held away from said opening, said release actuator being manually operable to release said spring arm of its free end up toward said opening;
a lancet blade holder on said free end of said spring arm;
a lancet blade carried by said holder;
a manually engageable element operatively connected to said spring arm and projecting outside said housing for manual engagement by the user to cock the spring arm in said stressed position where it is engaged by said release actuator;
said spring arm at its opposite end from said free end being anchored to said housing:
and said spring arm being preformed to an unstressed position in which its free end positions said lancet blade holder retracted down away from said opening and up from said stressed position in which it is held cocked by said release actuator;
and further comprising:
means, operable upon completion of said manual operation of the release actuator to release the spring arm, for locking the release actuator in a disabled position in which it cannot again hold said spring arm cocked in said stressed position.

4. A lancet according to claim 3, wherein:
said release actuator is movable substantially horizontally at the bottom of said housing to release the spring arm.

5. An automatic surgical lancet comprising:
a housing having a top wall with an opening therein for overlying engagement by the tip of a patient's finger;
an arm inside said housing having a free end which is movable up toward and down away from said top wall;
a lancet blade holder on said free end of said arm;

a lancet blade carried by said holder;

said arm being resiliently biased to position said lancet blade holder a short distance down from said top wall of the housing;

said arm being retractable downward against said resilient bias to position said lancet blade holder a substantial distance further down from said top wall;

and a release actuator for holding said arm cocked in its retracted position, said release actuator being located on said housing below said top wall, said release actuator being manually displaceable substantially horizontally to release said arm for upward movement of said lancet blade holder to carry said lancet blade into piercing engagement with the tip of a patient's finger over said opening in said top wall of the housing.

6. An automatic surgical lancet comprising:

a housing having a top wall for engagement by the tip of a patient's finger;

an arm inside said housing having a free end which is movable up toward and down away from said top wall;

a lancet blade holder on said free end of said arm;

a lancet blade carried by said holder;

said arm being resiliently biased to position said lancet blade holder a short distance down from said top wall of the housing;

said arm being retractable downward against said resilient bias to position said lancet blade holder a substantial distance further down from said top wall;

a release actuator for holding said arm cocked in its retracted position, said release actuator being manually displaceable substantially horizontally to release said arm for upward movement of said lancet blade holder to carry said lancet blade into piercing engagement with the tip of a patient's finger on said top wall of the housing;

and means, operable upon completion of said manual operation of the release actuator to release said arm, for locking the release actuator in a disabled position in which it cannot again hold said arm cocked in said retracted position.

7. A lancet according to claim 5, and further comprising:

a manually engageable element operatively connected to said arm and projecting outside said housing for manual engagement by the user to cock said arm in said retracted position where it is engaged by said release actuator.

8. A lancet according to claim 5, wherein:

said arm is a spring arm having its opposite end from said free end anchored to said housing;

and said spring arm is preformed to an unstressed position in which its free end positions said lancet blade holder retracted down away from said opening and up from said retracted position in which it is held cocked by said release actuator.

9. A lancet according to claim 8, wherein:

said housing has a molded central frame piece of deformable and resilient plastic material, and a pair of side pieces engaging the opposite sides of said central frame piece;

said frame piece has a top wall, a back wall joined to and extending down from said top wall, a bottom wall joined to and extending forward from the lower end of said back wall, a front wall joined to and extending down from said top wall, and a generally horizontal wall joined to and extending rearward from the lower end of said front wall above said bottom wall and having a locking element at its back end;

said spring arm is molded integral with said frame piece;

said lancet blade holder is molded integral with said spring arm and has a locking element for engagement with said locking element on said generally horizontal wall of the frame piece in said retracted position of the spring arm;

and said front wall of the frame piece is displaceable rearwardly at its lower end to disengage said locking element on said generally horizontal wall from said locking element on said lancet blade holder.

10. An automatic surgical lancet comprising:

a housing having a top wall for engagement by the tip of a patient's finger;

an arm inside said housing having a free end which is movable up toward and down away from said top wall;

a lancet blade holder on said free end of said arm;

a lancet blade carried by said holder;

said arm being resiliently biased to position said lancet blade holder a short distance down from said top wall of the housing;

said arm being retractable downward against said resilient bias to position said lancet blade holder a substantial distance further down from said top wall;

and a release actuator for holding said arm cocked in its retracted position, said release actuator being manually displaceable substantially horizontally to release said arm for upward movement of said lancet blade holder to carry said lancet blade into piercing engagement with the tip of a patient's finger on said top wall of the housing;

said housing having a molded central frame piece of deformable and resilient plastic material, and a pair of side pieces engaging the opposite sides of said central frame piece;

said frame piece having a top wall, a back wall joined to and extending down from said top wall, a bottom wall joined to and extending forward from the lower end of said back wall, a front wall joined to and extending down from said top wall, and a generally horizontal wall joined to and extending rearward from the lower end of said front wall above said bottom wall and having a locking element at its back end;

said spring arm being molded integral with said frame piece;

said lancet blade holder being molded integral with said spring arm and having a locking element for engagement with said locking element on said generally horizontal wall of the frame piece in said retracted position of the spring arm;

said front wall of the frame piece being displaceable rearwardly at its lower end to disengage said locking element on said generally horizontal wall from said locking element on said lancet blade holder;

said arm being a spring arm having its opposite end from said free end anchored to said housing; and said spring arm is performed to an unstressed position in which its free end positions said lancet blade holder retracted down away from said opening and up from said retracted position in which it is held by said release actuator;

and said side pieces of the housing having inwardly extending protrusions which guide said generally horizontal wall for movement substantially horizontally above said bottom wall of the housing.

11. An automatic surgical lancet comprising:

a housing having a top wall for engagement by the tip of a patient's finger;

an arm inside said housing having a free end which is movable up toward and down away from said top wall;

a lancet blade holder on said free end of said arm;

a lancet blade carried by said holder;

said arm being resiliently biased to position said lancet blade holder a short distance down from said top wall of the housing;

said arm being retractable downward against said resilient bias to position said lancet blade holder a substantial distance further down from said top wall;

a release actuator for holding said arm cocked in its retracted position, said release actuator being manually displaceable substantially horizontally to release said arm for upward movement of said lancet blade holder to carry said lancet blade into piercing engagement with the tip of a patient's finger on said top wall of the housing;

said housing having a molded central frame piece of deformable and resilient plastic material, and a pair of side pieces engaging the opposite sides of said central frame piece;

said frame piece having a top wall, a back wall joined to and extending down from said top wall, a bottom wall joined to and extending forward from the lower end of said back wall, a front wall joined to and extending down from said top wall, and a generally horizontal wall joined to and extending rearward from the lower end of said front wall above said bottom wall and having a locking element at its back end;

said spring arm being molded integral with said frame piece;

said lancet blade holder being molded integral with said spring arm and having a locking element for engagement with said locking element on said generally horizontal wall of the frame piece in said retracted position of the spring arm;

said front wall of the frame piece being displaceable rearwardly at its lower end to disengage said locking element on said generally horizontal wall from said locking element on said lancet blade holder;

said arm being a spring arm having its opposite end from said free end anchored to said housing; and said spring arm is preformed to an unstressed position in which its free end positions said lancet blade holder retracted down away from said opening and up from said retracted position in which it is held cocked by said release actutator;

a locking element extending up from said bottom wall of the frame piece;

and a locking element extending down from said generally horizontal wall and shaped to slide rearward over said locking element on said bottom wall and then move into locking engagement therewith when said generally horizontal wall is displaced rearward.

12. A disposable lancet comprising:

a generally rectangular housing having a molded central frame piece of deformable and resilient plastic material, and a pair of side pieces engaging the opposite sides of said frame piece;

said central frame piece having a top wall, a back wall joined to and extending down from said top wall, a bottom wall joined to and extending forward from the lower end of said back wall, a front wall joined to and extending down from said top wall, and a generally horizontal wall joined to and extending rearward from the lower end of said front wall above said bottom wall, said generally horizontal wall at its rear end having an upwardly extending locking element spaced in front of said back wall;

a spring arm of said deformable and resilient plastic material molded integral with said frame piece, said spring arm having one end thereof joined to said frame piece and having its opposite end free to move away from and toward said top wall;

a lancet blade holder on said free end of said spring arm, said holder having a locking element thereon for locking engagement with said locking element on said generally horizontal wall of the frame piece when said free end of the spring arm is retracted downward;

and a lancet blade carried by said holder;

said spring arm being preformed to an unstressed position in which it positions said lancet blade holder spaced below said top wall, said spring arm being stressed when its free end is retracted downward to engage said locking element on said holder with said locking element on said generally horizontal wall of the central frame piece;

said front wall being sufficiently flexible to permit its lower end to be manually pushed rearward to displace said generally horizontal wall rearward to disengage its locking element from said locking element on the lancet blade holder, thereby permitting said spring arm to move its free end upward and carry said lancet blade holder up to said top wall.

13. A lancet according to claim 12, wherein:

said central frame piece of the housing has a concave depression at said top wall for receiving the tip of a patient's finger and an opening at said depression for passing said lancet blade carried by said holder up into piercing engagement with the patient's finger tip.

14. A lancet according to claim 12, wherein:

at least one of said side pieces is formed with an arcuate slot;

and further comprising:

a cross piece attached to said spring arm and extending laterally outward therefrom through said slot for manual engagement to retract the free end of the spring arm.

15. A lancet according to claim 12, wherein:

said bottom wall of the frame piece has an upwardly projecting locking tooth;

and said generally horizontal wall has a downwardly extending locking tooth which is slidable rearwardly over said locking tooth on the bottom wall and into locking engagement with the latter when said lower end of the front wall is pushed rearward to release the spring arm.

16. A lancet holder according to claim 12, wherein:

said front wall of the frame piece has a forwardly offset segment at its lower end.

17. A disposable lancet comprising:
- a generally rectangular housing having a molded central frame piece of deformable and resilient plastic material, and a pair of side pieces engaging the opposite sides of said frame piece;
- said central frame piece having a top wall, a back wall joined to and extending down from said top wall, a bottom wall joined to and extending forward from the lower end of said back wall, a front wall joined to and extending down from said top wall, and a generally horizontal wall joined to and extending rearward from the lower end of said front wall above said bottom wall, said generally horizontal wall at its rear end having an upwardly extending locking element spaced in front of said back wall;
- a spring arm of said deformable and resilient plastic material molded integral with said frame piece, said spring arm having one end thereof joined to said frame piece and having its opposite end free to move away from and toward said top wall;
- a lancet blade holder on said free end of said spring arm, said holder having a locking element thereon for locking engagement with said locking element on said generally horizontal wall of the frame piece when said free end of the spring arm is retracted downward;
- and a lancet blade carried by said holder;
- said spring arm being preformed to an unstressed position in which it positions said lancet blade holder spaced below said top wall, said spring arm being stressed when its free end is retracted downward to engage said locking element on said holder with said locking element on said generally horizontal wall of the central frame piece;
- said front wall being sufficiently flexible to permit its lower end to be manually pushed rearward to displace said generally horizontal wall rearward to disengage its locking element from said locking element on the lancet blade holder, thereby permitting said spring arm to move its free end upward and carry said lancet blade holder up to said top wall;
- said side pieces near their lower ends having inwardly extending projections closely positioned above and below said generally horizontal wall to guide the latter for movement substantially horizontally.

18. A lancet holder according to claim 17, wherein:
- said housing has a concave depression at the top for receiving the tip of a patient's finger and an opening at said depression for passing a lancet blade carried by said holder up into piercing engagement with the patient's finger tip;
- said front wall of the frame piece has a forwardly offset segment at its lower end;
- said bottom wall of the frame piece has an upwardly projecting locking tooth;
- and said generally horizontal wall has a downwardly extending locking tooth which is slidable rearwardly over said locking tooth on the bottom wall into locking engagement with the latter when said lower end of the front wall is pushed rearward to release the spring arm;
- at least one of said side pieces formed with an arcuate slot;

and further comprising:
- a cross piece attached to said spring arm and extending laterally outward therefrom through said slot for manual engagement to retract the free end of the spring arm.

* * * * *